United States Patent
Nambakam et al.

(10) Patent No.: US 8,558,880 B2
(45) Date of Patent: Oct. 15, 2013

(54) WIRELESS OPERATING ROOM COMMUNICATION SYSTEM INCLUDING VIDEO OUTPUT DEVICE AND VIDEO DISPLAY

(75) Inventors: Vasudev Nambakam, San Jose, CA (US); John Shen, San Jose, CA (US); Joshua Talbert, San Jose, CA (US); Amit Mahadik, San Jose, CA (US)

(73) Assignee: Stryker Corporation, Kalamazoo, MI (US)

( * ) Notice: Subject to any disclaimer, the term of this patent is extended or adjusted under 35 U.S.C. 154(b) by 261 days.

(21) Appl. No.: 12/998,425

(22) PCT Filed: Oct. 30, 2009

(86) PCT No.: PCT/US2009/005934
§ 371 (c)(1),
(2), (4) Date: Apr. 18, 2011

(87) PCT Pub. No.: WO2010/059179
PCT Pub. Date: May 27, 2010

(65) Prior Publication Data
US 2011/0193949 A1 Aug. 11, 2011

Related U.S. Application Data

(60) Provisional application No. 61/199,921, filed on Nov. 21, 2008.

(51) Int. Cl.
*A61B 1/04* (2006.01)
*A62B 1/04* (2006.01)
*A61B 1/06* (2006.01)

(52) U.S. Cl.
USPC .............................. 348/74; 348/65; 600/249

(58) Field of Classification Search
USPC ....................... 348/65–77; 600/249
See application file for complete search history.

(56) References Cited

U.S. PATENT DOCUMENTS

| 7,257,158 B1 | 8/2007 | Figueredo et al. |
| 2001/0015754 A1* | 8/2001 | Nakashima et al. ............ 348/65 |

(Continued)

FOREIGN PATENT DOCUMENTS

| EP | 1 769 726 A2 | 4/2007 |
| WO | WO 2008/063565 A2 | 5/2008 |

OTHER PUBLICATIONS

International Preliminary Report on Patentability dated Jun. 3, 2011 for corresponding PCT Application No. PCT/US2009/005934.

(Continued)

*Primary Examiner* — David Czekaj
*Assistant Examiner* — Tsion B Owens
(74) *Attorney, Agent, or Firm* — Flynn, Thiel, Boutell & Tanis, P.C.

(57) ABSTRACT

A wireless operating room communication system provides wireless transmission of video signals from a wireless camera or a wireless transmitter unit to a portable wireless display unit. A wireless multiple device control unit is in wireless communication with the transmitter unit, the display unit, and a plurality of surgical devices disposed within the operating room. Each of the surgical devices has a video receiver to obtain a video signal to synchronize the devices and units. The video transmitter unit has a video transmitter and the other units or devices have a non-video transmitter. The arrangement enables transmission of device control signals on the same channel as the video signal. In response to changes in bandwidth, the video transmitter unit reduces the video signal to enable transmission thereof to the video display unit, while maintaining robustness of the control signals.

20 Claims, 6 Drawing Sheets

(56) References Cited

U.S. PATENT DOCUMENTS

| | | |
|---|---|---|
| 2006/0116667 A1 | 6/2006 | Hamel et al. |
| 2007/0070195 A1 | 3/2007 | Abe |
| 2007/0098063 A1 | 5/2007 | Reznic et al. |
| 2007/0177670 A1 | 8/2007 | Elnathan et al. |
| 2008/0139881 A1* | 6/2008 | Cover et al. .................. 600/103 |
| 2008/0207127 A1* | 8/2008 | Ijichi et al. .................. 455/41.2 |

OTHER PUBLICATIONS

International Search Report and Written Opinion dated Jan. 28, 2010 for corresponding PCT Application No. PCT/US2009/005934.

* cited by examiner

WIRELESS OPERATING ROOM COMMUNICATION SYSTEM INCLUDING VIDEO OUTPUT DEVICE AND VIDEO DISPLAY

CROSS REFERENCE TO RELATED APPLICATION

This application is the National Stage of International Application No. PCT/US2009/005934, filed Oct. 30, 2009, which claims the benefit of U.S. Provisional Application Ser. No. 61/199 921, filed Nov. 21, 2008, which is incorporated herein by reference in its entirety.

FIELD OF THE INVENTION

This invention is directed to a wireless operating room communication system that transmits data signals, audio signals and video signals among devices provided in an operating room.

BACKGROUND OF THE INVENTION

The remote control of application devices connected to each other through hard-wire connections is well known in an operating room. For instance, a controller having voice-activation and a touchscreen control device is capable of selectively controlling a plurality of surgical devices in an operating room. Such surgical devices include a hand-held powered cutting device with an irrigation device, an electrocautery device, a digital camera, an image capture unit used to record and manage images obtained by the camera, a video display, a light source for providing light to a surgical site, an insufflator device, room lights and other operating room tools and equipment.

The above arrangement, however, leads to a plurality of connecting cables disposed throughout an operating room. The cables interfere with work areas of a surgeon or other medical personnel. Further, the cables limit the movement of surgical devices, including video displays, within the operating room.

The use of a communication bus in an operating room for communication between a plurality of operating room devices is known. A bus arrangement, however, merely reduces the number of cables provided throughout an operating room and thus does not completely address the issues caused by the presence of cabling.

The use of wireless remote controllers, such as a wireless touch screen to provide inputs to an operating room controller, or a wireless foot switch for providing control signals to devices in an operating room is known. These operating room communication systems typically include a wireless transmitter only in the remote control device and do not transmit wireless video signals.

Video data in an operating room typically is transmitted over hard-wire connections from a camera to a video display monitor or to an image capture unit that stores, records and manages the images output from the camera.

The use or practice of providing a completely wireless operating room communication system including video signal transmission has not been completely realized. As set forth in commonly-owned U.S. Patent Publication No. 2008/0139881, filed Nov. 15, 2007, the disclosure of which is hereby incorporated by reference, use of a wireless endoscope having a wireless transmitter mounted thereon is known. One reason wholly wireless operating room systems are not currently in use, is the inability to provide communication signals and video signals together on a broadcast channel due to potential errors in transmission of the signals caused by electromagnetic interference, along with a lack of bandwidth (high data rate) due to the typically large bandwidth (high data rate) required for video signals.

Many video images collected and displayed in an operating room environment do not require particularly sensitive resolution. Minor degradation of image quality generally is not significant for displays used during surgical procedures.

The wireless arrangement according to the invention combines data or control signals with video signals while ensuring delivery of control signals in all situations, even at the expense of occasional loss of portions of video signals and thus loss of video signal quality.

Further, the invention provides a video camera or other video device in an operating room having a wireless video connection with portable battery powered video displays provided therein. Such arrangements allow a user to freely move the video displays throughout the entirety of an operating room during a surgical procedure.

The invention also provides a completely wireless operating room system for surgical tools, a video camera, a video display, and other devices provided in an operating room by combining control command signals, audio signals and video signals for wireless transmission on a single communication channel.

The invention prioritizes the different communication signals transmitted on or with video signals. Control signals and audio signals are transmitted during blanking periods or blanking intervals of a video signal. The control command signals are provided with the highest priority techniques, such as retransmission of data or bit encoding to ensure communication accuracy. Audio signals, such as voice commands transmitted from a wireless microphone, are provided with a lesser degree of priority and thus less accurate signal transmission than high priority control command signals.

Further, video signals have a low latency between sensing by an image sensor of a digital camera and display. For example, video signals are minimally encoded with most significant bits and least significant bits. The least significant bits are lost first due to electromagnetic interference or other transmission issues.

Further, the invention automatically changes the communication channel utilized by the operating room wireless system when the communication channel has a signal to noise ratio (SNR) or a peak signal to noise ratio (PSNR) from electromagnetic interference that prevents the system from operating effectively.

Certain terminology will be used in the following description for convenience and reference only, and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the arrangement, and designated parts thereof. Said terminology will include the word specifically mentioned, derivatives thereof, and words of similar input.

DETAILED DESCRIPTION

Figure 1:
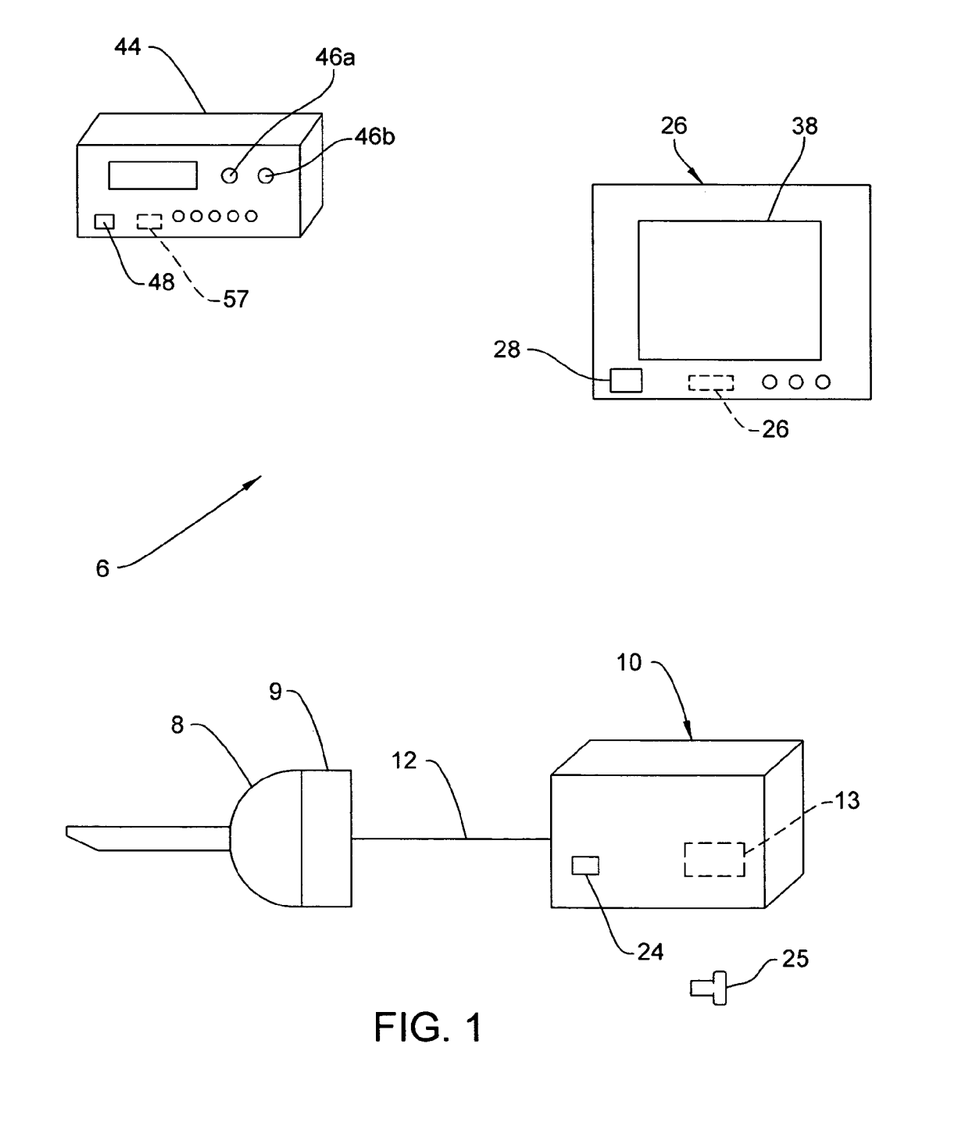
FIG. 1 shows a wireless operating room system including a wireless video transmitter unit, a wireless video display unit and a wireless control unit.

FIG. 1 shows a wireless operating room control system 6 including an endoscope 8, a camera head 9 and a wireless video transmitter unit 10 connected to the camera head 9 by a video cable 12.

Figure 2:
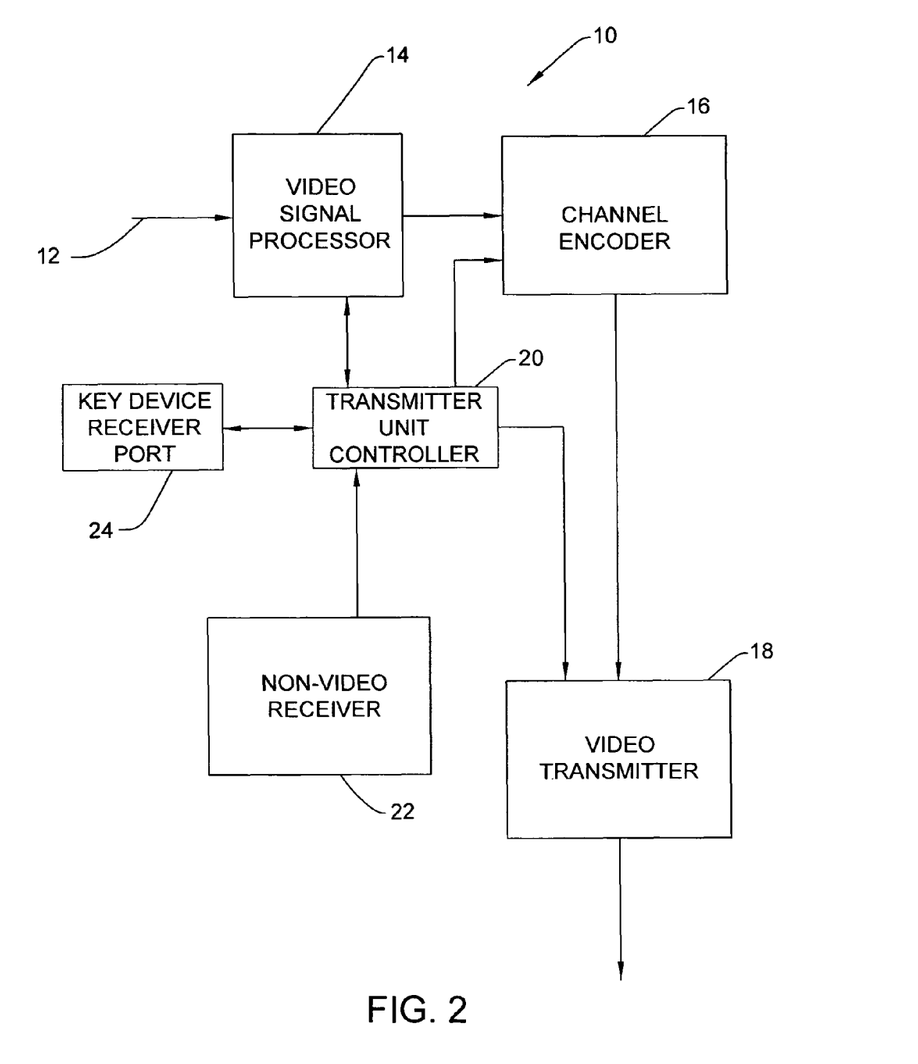
FIG. 2 is a block diagram of the wireless video transmitter unit shown in FIG. 1.

As shown in FIG. 2, the wireless video transmitter unit 10 receives an image output from the camera head 9 carried on the video cable 12. A portable battery 13 provides power to the wireless video transmitter unit 10.

Signal processor 14 of the transmitter unit 10 processes the image signal and provides the output to a channel encoder 16. The channel encoder 16 provides an output to broadcast video transmitter 18. Transmitter unit controller 20 of the wireless video transmitter unit 10 connects to and communicates with the signal processor 14. The unit controller 20 also connects to the channel encoder 16, video transmitter 18 and a non-video transmitter unit receiver 22. Key device receiving port 24 connects to the controller 20. A key device 25 is provided for insertion into port 24.

Figure 3:
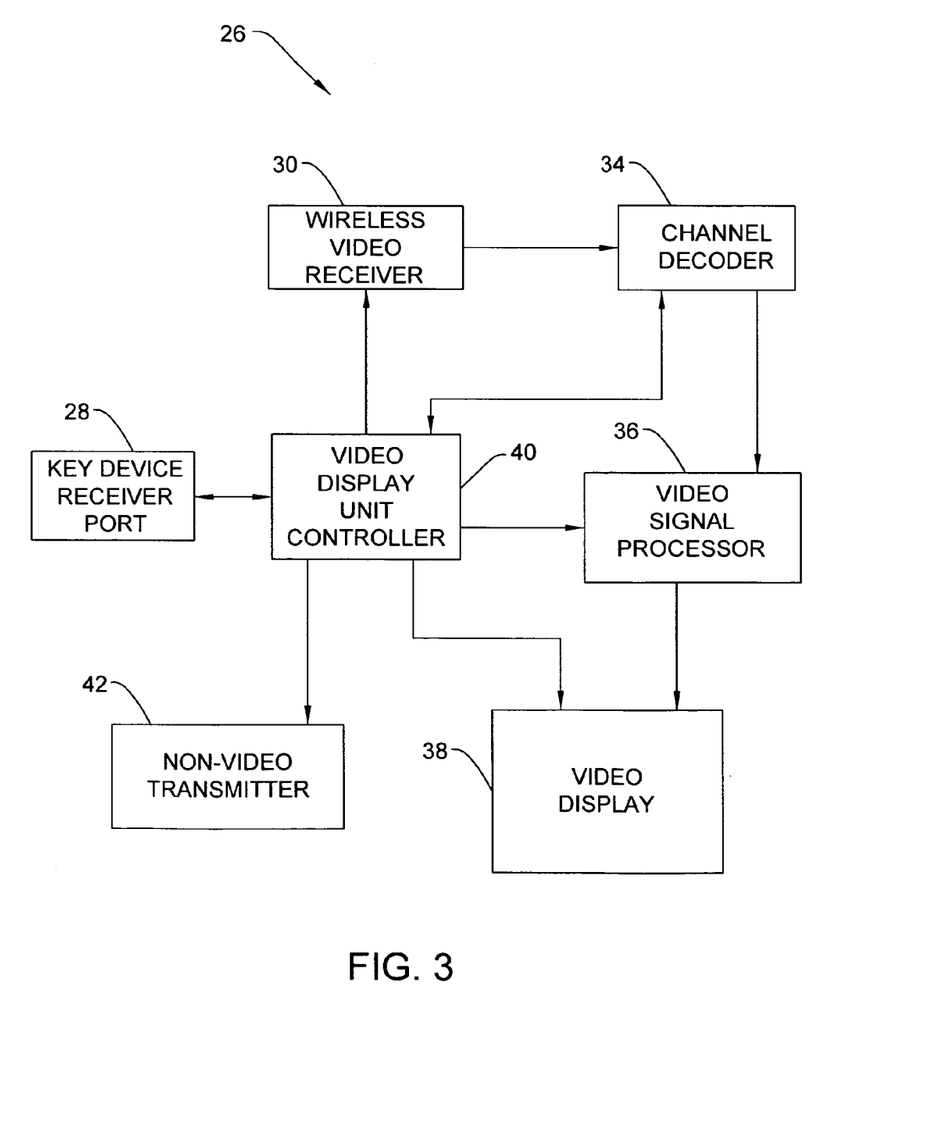
FIG. 3 is a block diagram of the wireless video display unit shown in FIG. 1.

The portable wireless surgical video display unit 26 shown in FIG. 1 includes a key device receiving port 28. As shown in FIG. 3, the wireless video display unit 26 includes a wireless video receiver 30 and a signal processor 32 connected to a channel decoder 34. The channel decoder 34 connects to a digital image processor 36, which provides a video output to a video display 38. A power supply, such as portable battery 39 is provided within the wireless video display unit 26 as shown in FIG. 1 for powering the wireless video display unit.

Video display unit controller 40 connects to the key device receiver port 28, signal processor 32, channel decoder 34, digital image processor 36 and video display 38. Further, the video display unit controller 40 provides an output to a non-video transmitter 42.

FIG. 1 illustrates a multiple device control unit 44 having surgical device connection ports 46a, 46b and a key device receiver port 48. As illustrated in the block diagram of FIG. 4, the multiple device control unit 44 includes a video receiver 59 which provides an output to a video signal timing and control signal processor 52 that includes a channel decoder 53. The video signal timing and control signal processor 52 provides an output to a multiple device controller 54 that is connected to the key device receiver port 48. The multiple device controller 54 also connects to a non-video transmitter 56 for communicating control signals. In some embodiments, portable battery 57 provides power to the multiple device control unit 44.

Synchronization

In order for the wireless operating room control system 6 having video transmission to operate properly, all of the operating room devices, such as the wireless video transmitter unit 10, wireless video display unit 26 and multiple device control unit 44 shown in FIG. 1 must identify and recognize each other. This process is referred to as synchronization.

In one embodiment, a key device 25 shown in FIG. 1 is inserted into the respective key device receiving ports 24, 28, 48 of the operating room units. The key device 25 provides an initial operating channel for the plural units or devices. Thus, the transmitter unit controller 20 of the wireless transmitter unit 10 knows what input to provide to the channel encoder 16 to encode an image output that is provided to the video transmitter 18 for broadcast.

At the same time, the video display unit controller 40 and the multiple device controller 54 receive the operating channel and other data parameters from the key device 25, which stores the initial operating channel of the wireless transmitter unit 10 and other parameters.

To synchronize, the wireless video display unit 26 shown in FIG. 3 receives the wireless video signal at video receiver 30 and provides the signal to channel decoder 34. Channel decoder 34 decodes the video signal and provides the signal to video signal processor 36, which displays the video signal on video display 38. Further, channel decoder 34 provides the decoded signal to video display unit controller 40.

Figure 4:
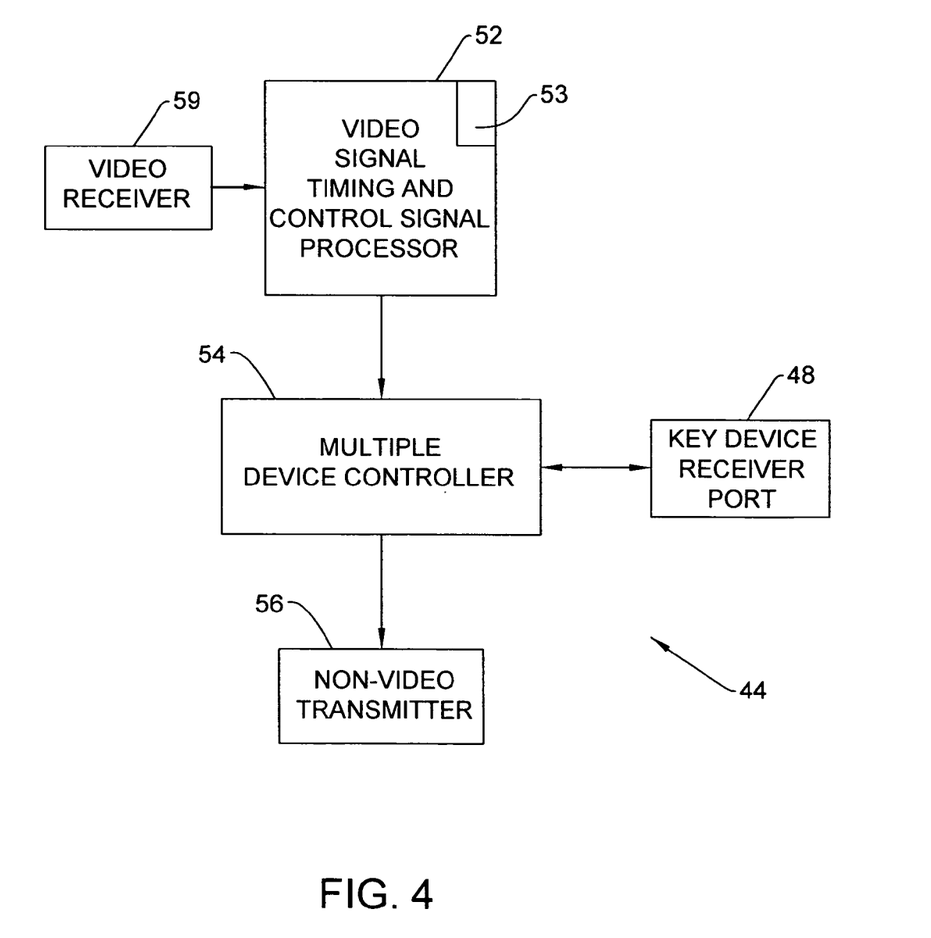
FIG. 4 is a block diagram of the wireless multiple-device control unit shown in FIG. 1.

With regard to the multiple device control unit 44 shown in FIG. 4, the video receiver 60 receives the broadcast video signal and provides same to video signal timing and control signal processor 52. The multiple device controller 54 receives the encoding channel and other operating information from the key device 25 inserted into the device receiving port 48. Thus, the multiple device controller 54 is aware of the channel that the video signal is being provided on and provides such data to the timing and control signal processor 52. The timing and control signal processor 52 then provides an output to the multiple device controller 54 including the necessary details of the video signal for display purposes.

Synchronization of the wireless transmitter unit 10, the wireless video receiver unit 26 and the multiple control device unit 44, as well as additional devices (not shown) is necessary for operation of the system, since the control signals from the synchronized units are transmitted along with the video signals.

Channels and Sub-Channels

According to one exemplary embodiment, the wireless operating room system with video signal transmission utilizes ultra wide band (UWB) technology to wirelessly transmit a video signal from the wireless transmitter unit 10 to the wireless video display unit 26. UWB is a wireless radio technology designed for transmitting data over short distances (up to 20 meters) at very high data rates (500 plus MBps). To accomplish high data transmission rates, UWB transmits over a wide range of radio spectrum using a series of very narrow and low-power pulses. Typically, UWB transmissions exceed the lesser of 500 MHz or 20% bandwidth within the 3.1 to 10.6 GHz spectrum.

One specific UWB-based standard that can be affectively utilized in the current embodiment is known as Multi-band Orthogonal Frequency Division Multiplexing (MB-OFDM). As a result of transmitting data simultaneously over multiple carriers spaced apart at precise frequencies, the MB-OFDM standard produces wireless transmissions that are resilient to RF interference and multi-path effects. Such arrangements are disclosed in U.S. Patent Publication No. 2007/0098063, filed Oct. 20, 2006, and U.S. Patent Publication No. 2007/0177670, filed Jan. 14, 2007, the disclosures of which are hereby incorporated by reference.

To enable operation of multiple units in an operating room, wherein a unit outputs video signals, as well as control signals, a two or three sub-channel arrangement is provided. These are virtual sub-channels not necessarily correlated to physical channels, such as frequency, time, or space-time. A main sub-channel carries video signals from the wireless video transmitter unit 10 to the wireless video display unit 26 and other devices.

A second sub-channel carries control signals between and among all of the units 10, 26, 44 and additional devices, such as insufflators, electrocautery probes, endoscope light sources, endoscope cameras and image capture units that have a similar control structure/arrangement to the multiple device control unit 44 illustrated in FIGS. 1 and 4. Thus, in the multi-channel arrangement, a control signal sub-channel defined by a small portion of the channel provides for the transmission of control signals among all of the wireless units and wireless surgical devices disposed in the operating room. Therefore, the multiple device control unit 44 communicates with the above listed surgical devices independent from communication with the wireless transmitter unit 10 and the wireless video display unit 26, even though the multiple device control unit 44 is capable of controlling, such as turning on and off, the units 10, 26.

In some embodiments that include a wireless microphone for providing audible command signals, a sub-channel is provided for audio signal transmission. For instance, a battery powered wireless microphone (not shown) having a video signal receiver can process audible signals that are sensed by the video signal timing and control signal processor 52 show in FIG. 4. The video signal timing and control signal processor 52 has a channel decoder 53 that decodes at least a portion of the video signal that is carrying audible information. The audible information is used by the multiple device controller 54 for controlling select ones of the multiple devices listed above.

Data Transmission

Data transmissions of control signals over or with the video signals are provided in a number of different ways. Multiplexing of digital data signals is well known and can be performed, for example, in time, frequency or space.

Figure 5:
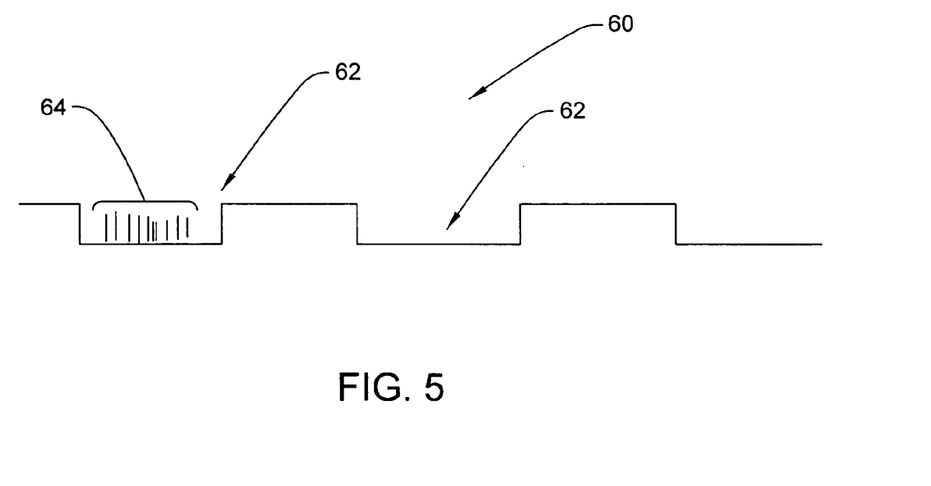
FIG. 5 illustrates a portion of a video signal that includes data signals.

Another approach is sending control signals with the video signals 60 during blanking intervals 62 as shown in FIG. 5. The control signal 64 may be from any one of the units or the devices provided in an operating room.

In some embodiments the bandwidth (data rate) is large enough to accommodate the video signal and a significant amount of additional data.

Additional known data processing arrangements allow for the sharing of a channel including a video signal with control signals and/or units and thus will not be discussed further herein. For instance, digital television broadcasts provide both video and audio signals thereon.

Priority Arrangement

For the above system to function properly on a single video channel, an error priority scheme must be provided for command control signals 64 and a time priority scheme must be provided for video signals 60.

The control signals 64 have a high error priority. Control signals 64 sent from the multiple device control unit 44 to individual devices, for example, must be detected without error. Thus, the control signals 64 are encoded, retransmitted or otherwise provided with appropriate data correction encoding arrangements to ensure data thereof is not lost during wireless transmission.

A second category of an error priority scheme is directed to the transmission of audio signals for embodiments that transmit and process audible control commands. The audio or voice signals have an error priority scheme that is less accurate than the control signal error priority scheme. The audio signals typically are verbal commands received by a wireless microphone (not shown) and transmitted therefrom to the multiple device control unit 44 for voice recognition analysis. In some embodiments, forward error correction (FEC) is used to ensure accuracy for audio signals.

Turning to video signals 60, the video signals require a time priority scheme to display video in a short duration after detection by an image sensor. Thus, the latency of video signals between the camera and the video display 38 is of great importance.

Low Latency/Time Priority

Known prior art video systems sometimes provide buffer storage of various frames of data so that data transmission can be delayed, when unavailable, and then transmitted to a video display or the like. Other arrangements utilize data compression, which results in a significant time delay between data compression and data decompression, before display of the video signal. For some purposes, such as television transmission, the delay is not significant.

In an operating room setting, however, a surgeon moving his hands and tools within an operating room needs essentially immediate feedback to a video display to comfortably perform surgery.

The wireless operating room communication system 6 provides low latency for the video signals 60 being transmitted from the wireless transmitter unit 10 to the wireless video display unit 26 as follows. The image output received from video cable 12 is processed by video signal processor 14 of the transmitter unit 10 in a quick manner, as minimal video signal encoding occurs. Further, frame buffers are not provided in the signal processor 14 to store multiple frames of video image data. The video signal is provided to channel encoder 16 and then broadcast via video transmitter 18 to, for example, the wireless video display unit 26.

The wireless video receiver 30 of the wireless video display unit 26 receives the video signal 60 and provides same to a channel decoder 34 that decodes the video signal 60. The decoded signal is provided to video signal processor 36 which displays the video signal as a video image on video display 38.

By not providing frame buffers that store multiple frames of video signals for transmission from the wireless transmitter unit 10, video signals 60 are advanced quickly from the transmitter unit to the video display unit 26.

For instance, high definition video signals are typically sensed at a frame rate of 60 frames per second and thus at a frame rate of 0.0166 seconds for each frame. In one embodiment, minimal coding of the video signal leads to a time delay of approximately four milliseconds from the time the image is read by a camera image sensor until the time the image is displayed on video display 38. Thus, the latency or time delay of the transmitted video signal is less than 30% of the scanning time for each frame of a high definition image sensor of a camera disposed in the camera head 9. In some embodiments, the transmitter unit 10 begins sending video signals from a frame before the entire frame is read.

With regard to high speed cameras, which have an even greater frame rate, the invention contemplates maintaining the same percentage rate of data transfer or a lower rate for the latency of the video signals.

The above arrangement enables the wireless operating room communication system 6 to operate on one channel while providing data signals, audio signals and video signals thereon.

Change of Bandwidth/Data Rate

In operation, the bandwidth or MB per second (MBps) of data transfer between the wireless transmission unit 10 and the video display unit 26 varies according to electromagnetic interference and other conditions. In some known embodiments, a rate of more than 500 MBps is achieved. The video display unit 26 and the multiple device control unit 44 are capable of determining a transmission rate and of utilizing the respective non-video transmitters 42, 56 to provide control signals to the wireless transmitter unit 10. The transmitter unit 10 processes the control signals to determine the amount that data rate has decreased, and thus the amount of data being sent that must be reduced. On the other hand, this information is used to either increase transmission power, change coding technique, or move to another channel.

In most embodiments, the size of the sub-channels for the control signals and other operating data do not change in response to variations in the data rate. The sub-channels are maintained, as the control signals 64 are such a small part of the overall data channel. Further, in instances where audio signals are present, the amount of bandwidth that the signals require is negligible, and thus the audio signals are not changed in terms of data transmission due to a slowing of the data transmission rate.

The video signals 60, however, are changed in accordance with the bandwidth or data rate of the overall operating room communication system 6. Variations in the data rate of the broadcast video signals 60 require the video transmitter unit 10 to output less video data at particular times.

In other embodiments, the modulation/coding system is designed such that the "effective" bandwidth inherently lowers, with lesser channel quality over some levels of degradation, before the transmitter modulation/coding scheme is modified.

Channel Switching

Changes in the data rate, especially the loss of data rate or bandwidth, provide a challenge with respect to the wireless operating room system. The main operating approach to loss of data rate is as follows. The wireless transmitter unit 10 receives control signals from other units 26, 44 at non-video receiver 22 that are provided to the controller 20 thereof.

During operation of the wireless operating room system 6, if an unacceptable amount of interference is present on the selected channel of the wireless link, the units and devices are capable of communicating that the channel is not available and after a set time period a switch is made to a new channel and resynchronization occurs.

Operating Room Control System

Figure 6:
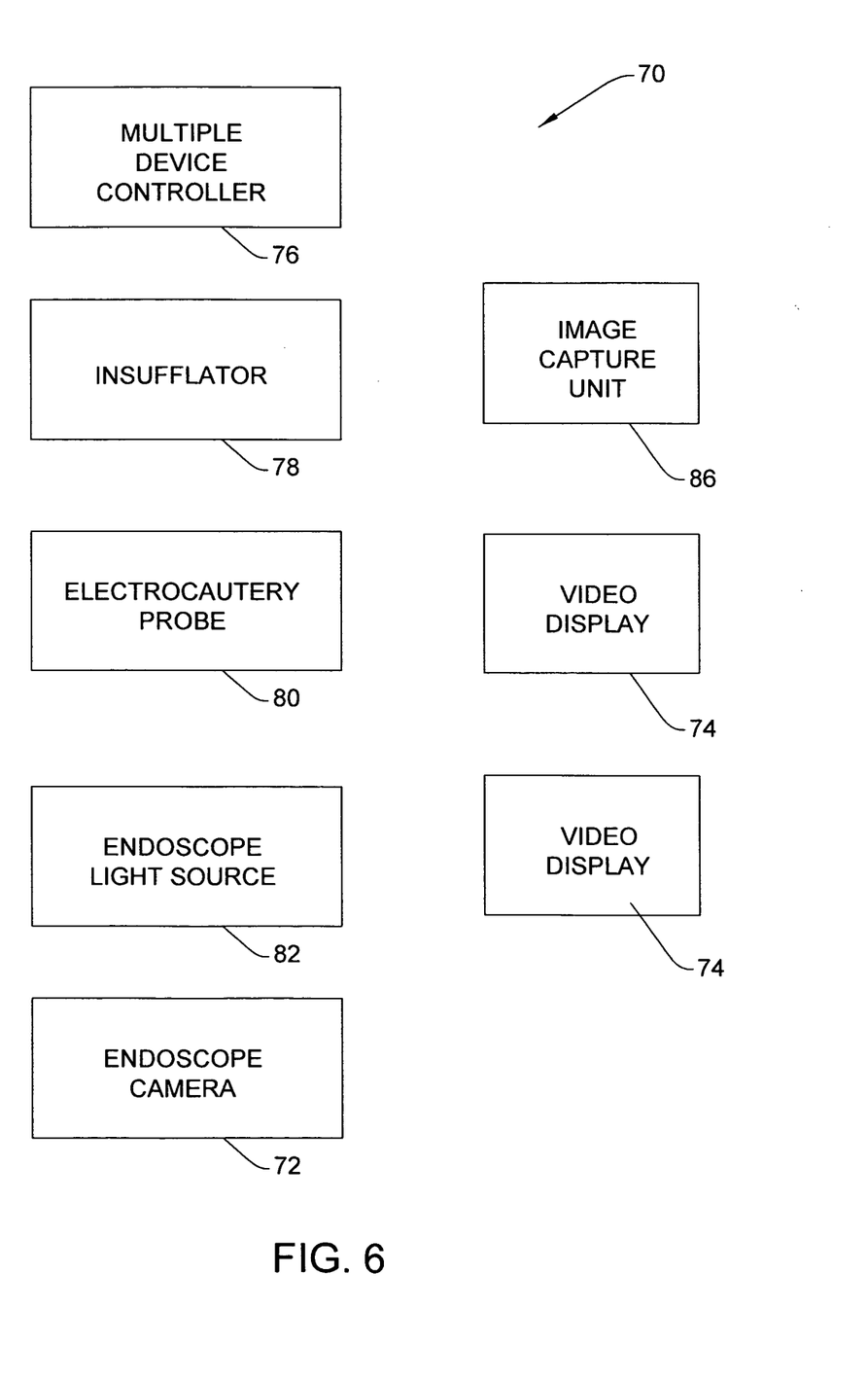
FIG. 6 is a block diagram of an embodiment including a plurality of surgical devices and video units provided with wireless communication.

FIG. 6 shows a wireless operating room communication system also acting as an operating room control system 70 for providing wireless communication between a plurality of devices, including an endoscope camera 72 and video displays 74 in an operating room. The wireless operating room system 70 includes a multiple device controller 76, an insufflator 78, and electrocautery probe 80, an endoscope light source 82, an endoscope camera 72, an image capture unit 86 and wireless surgical video displays 74. Each of the devices shown in FIG. 6 includes a transmitter and a non-video receiver, except for the image capture unit 86 and the video displays 74, each of which includes a video receiver. In some embodiments, the multiple device controller 76 also receives video signals 60.

Many of the devices illustrated in FIG. 6 only transmit control signals and also only act upon control signals that are processed therein.

In one embodiment, the endoscope camera 72 has integrated therein a transmitter that transmits video signals and the wireless surgical video displays 74 receive the video signals and process same in a similar manner as discussed above with respect to the embodiment of FIGS. 1-4. The image capture unit 86 includes a video receiver that receives video signals and also includes a video transmitter that may wirelessly transmit video signals on a different channel to a remote device.

In some embodiments, the wireless operating room control system 70 shown in FIG. 6 includes key receiving ports (not shown) for each of the devices. The key receiving ports receive key device 25 in order to ensure that all of the devices begin operation on the same channel of a wireless link signal.

In the embodiment of FIG. 6, however, each of the surgical devices has the same default channel for signal transmission. At start up, the devices 72, 74, 76, 78, 80, 82 and 86 communicate with each other on the default communication channel. In a handshake-type arrangement, the multiple device controller 76 determines the presence of each of the devices 72, 78, 80, 82 and 86, and the wireless video displays 74.

When the devices 72, 74, 76, 78, 80, 82 and 86 are synchronized initially, if the desired default channel has a large amount of interference or a low signal to noise ratio, the devices eventually switch to a different predetermined channel after a predetermined time in order to synchronize.

During and after synchronization, the transmitters of the insufflator 78, electrocautery probe 80 and endoscope light source 82 merely transmit signals for receipt by the multiple device controller 76 so that the multiple device controller knows of their existence for control purposes. In operation, the multiple device controller 76 sends data control signals 64 that are read by the respective devices 78, 80 and 82 for control thereof. The receivers of the devices 78, 80 and 82 disregard the video signal, except for synchronization purposes, when reading the control signals from the multiple device controller 76.

The multiple device controller 76 also provides control signals 64 to operate the endoscope camera 72, which sends video signals to the image capture unit 86 and the video displays 74.

The multiple device controller 76 sends data control signals 64 to operate the image capture unit 86 to capture images or record the video signal.

FIG. 6 shows two wireless video displays 74. In some embodiments, up to six video displays 74 may also receive video signals from the wireless endoscope camera 72.

Turning to the video signals 60, as in the embodiment of FIGS. 1-4 the loss of video image data is of less concern with respect to the wireless operating room communication system 6 as compared to loss of control signals. If portions of video image signals 60 are degraded, the wireless surgical video display 74 or the image capture unit 86 remains with an acceptable video image for viewing by a user, as the image change is not perceptible as a result of the signal degradation.

Central Wireless Link

In a central wireless link embodiment, the wireless video transmitter unit 10 shown in FIG. 2, or the endoscope camera 72 including an integrated video transmitter and a non-video receiver shown in FIG. 6, are provided as a wireless link for the operating room communication systems 6, 70.

In the FIG. 6 embodiment, the non-video receiver of the endoscope camera 72 receives wireless control signals from one or more of the wireless devices 76, 78, 80, 82 and 86. The wireless control signals typically are in a data packet type of format.

A data processor of the endoscope camera 72 reads the control signals and determines which of the devices 76, 78, 80, 82 and 86 that the control signal is intended for. The endoscope camera 72 then broadcasts the control signal along with the video signal. The control signal typically is provided as a data packet that is addressed to the intended device.

For example, when an operator provides an input command to the multiple device controller 76 to power the electrocautery probe 80, the command is delivered as follows. The multiple device controller 76 receives and processes the input command. The multiple device controller 76 then wirelessly outputs a wireless control signal including the electrocautery probe as a destination and including a power probe command.

The endoscope camera 72 receives the control signal from the multiple device controller 76 and processes the control signal. The processed signal is provided with the electrocautery probe 80 as a destination.

The endoscope camera 72 then broadcasts the control signal with a video signal. A video receiver of the electrocautery probe 80 receives the video signal and the control signal addressed thereto. The electrocautery probe reads the power probe command from the control signal and powers the probe.

In the above described arrangement, the non-video receiver and the video transmitter of the endoscope camera 72 act as a wireless link for transmitting control signals between devices 74, 76, 78, 80, 82 and 86. In some embodiments, the endoscope camera 72 of FIG. 6 is replaced with the camera head 9 and the separate wireless transmitter unit 10, having video transmitter 18 and non-video receiver 22 as shown in FIGS. 1 and 2.

Alternatives

While the key device 25 described above with respect to FIG. 1 is easy to implement, other embodiments also providing a manual key device to assist in synchronizing the devices are also contemplated. In some embodiments, an infrared remote, USB sticks, or RFID elements are provided to inform the various devices of a start up channel and other information for synchronization thereof.

A USB stick is an easy option to implement. The user, however, must be careful to ensure that the USB stick is not overwritten with any other data that would destroy the synchronization function thereof.

In embodiments where the units and devices of the operating room communication systems 6, 70 stay in a surgical operating room and are never removed therefrom, the channel of the wireless link may be preselected and remain the same during every use of the wireless operating room communication system. Thus, no key device 25 is required in such an embodiment.

As discussed above, however, where different devices are taken to and from an operating room, a synchronization function of some type, even if manually provided with a key device 34, is necessary.

In one embodiment the bits per pixel of the video data are prioritized in a simple and fast manner so that, for example, the most significant bit gets the highest priority and the lowest significant bit gets the lowest priority. Thus, if channel characteristics start to deteriorate, then first the lowest significant bits of the video data are lost. If the channel capacity keeps reducing, further video data is lost until the wireless operating room communication system switches to a sensed open channel.

In another embodiment, the wireless operating room communication systems 6, 70 provide software upgrades to every wireless transmitter/receiver in communication with the multiple device control unit.

In some embodiments, devices communicate with each other without sending a control signal to the multiple device controller 76. For instance, in one embodiment a wireless foot switch sends control signals directly to selected ones of the various devices 72, 74, 78, 80, 82 and 86.

In some embodiments, at start up, the devices 72, 74, 76, 78, 80, 82 and 86 of the wireless operating control system 70 automatically determine the best available channel and synchronize to that channel. In this embodiment, no key device 25 is necessary.

Since the wireless operating room communication systems 6, 70 typically only provide video signal transmissions from one transmitter, the communication is asymmetric with respect to the video transmitter. All available bandwidth is used to effectively communicate video from source to display.

The use of non-video transmitters for various devices and units reduces the overall cost of the circuitry for the operating room communication system. Each non-video transmitter then would utilize just the control channel for communicating information to the overall system.

Dual Channel Arrangement

In some embodiments, the wireless operating room communication system includes an image output unit that outputs video signals 60. In some embodiments, the image output unit includes a DVD player or other image storage device to provide images or a computer network (not shown) to provide images from a remote storage device.

In a multiple video channel arrangement, the endoscope camera 72 provides a video signal to a first one of the video displays 74. An image output unit transmits a second wireless video signal on a second channel to a second video display 74. In one embodiment, the second channel can be selected by the use of a key device 25 that is received in key receiving ports of the image output unit and a video display key port of the second video display. The data provided on the key device 25 synchronizes the devices that receive the key device on a different channel from a first endoscope camera channel. The second video signal typically is provided on a second channel having more noise than the first channel displaying the image from the endoscope camera 72.

In a multiple video channel arrangement, the multiple device controller 76 includes first and second key receiving ports. The key receiving ports enable devices selected with and synchronized by a first key device and devices selected with and synchronized by a second key device to communicate with the multiple device controller 76 over separate channels. In this manner, the multiple device controller 76 communicates with and controls every device in the wireless operating room control system 70, even in instances where one set of devices in an operating room is not capable of communicating with another set of devices due to their signal transmission being provided on different channels.

In some embodiments a single key receiving port detects and stores information from each of two key devices for use by the multiple device controller 76.

During a surgery in an operating room, in one embodiment the wireless operating room system 70 shows one set of images, such as previous patient images obtained over a network from a remote storage unit on a first wireless video display 74. At the same time, images from the endoscope camera 72 are displayed on a second wireless video display 74. In this manner, a surgeon may utilize recorded images to assist in a surgical procedure performed with an endoscope camera 72.

Other embodiments include a software program that divides operating room devices into a first set of operating room devices corresponding to the arrangement illustrated in FIG. 6, and a second set of devices including an image output unit along with a corresponding video display that operate on a second different wireless channel independent from the channel of the other devices in the operating room. The second wireless channel, if necessary due to a high signal to noise ratio (SNR), switches between a plurality of channels that differ from a first plurality of channels that the first video transmitter unit is capable of switching between.

In some embodiments the video signal channels have a bandwidth of 20 MHz. In other embodiments the bandwidth is 40 MHz. Further, other bandwidth values are contemplated.

Various wireless tools and devices can be provided so that the wireless operating room control system 70 is configured for arthroscopy, laparoscopy, ENT, hysteroscopy and cystoscopy procedures.

In some embodiments, the wireless operating room communication systems are utilized with high definition wireless video transmission units having an input resolution of 1280× 720 at either 60 Hz or at 50 Hz. In another embodiment, the video transmission units have an input resolution of 1920× 1080 at 60 Hz or at 50 Hz. Further, high definition arrangements having even greater input resolution are contemplated for the wireless transmitter unit and for the wireless video displays or other wireless video receiving devices, such as image capture units.

With regard to transmission protocols, the wireless operating room system can operate with Bluetooth, WiFi, wireless USB or other arrangements.

Although particular preferred embodiments of the invention are disclosed in detail for illustrative purposes, it will be recognized that variations or modifications of the disclosed apparatus, including the rearrangement of parts, lie within the scope of the present invention.

What is claimed is:

1. A wireless operating room communication system comprising:
    a wireless multiple device control unit including a non-video transmitter and a receiver;
    an endoscope camera and a wireless video transmitter unit for broadcasting video signals;
    at least one wireless surgical device, said at least one surgical device including a non-video transmitter and a receiver; and
    a wireless video display unit including a wireless video receiver for receiving and displaying video signals from the wireless video transmitter unit;
    wherein the multiple device control unit and the at least one said wireless surgical device are configured to receive and synchronize with the video signals broadcast by the wireless video transmitter unit, and
    wherein the at least one wireless surgical device and the multiple device control unit are configured to transmit control signals on the same frequency channel as the video signals transmitted by said wireless video transmitter unit.

2. The wireless operating room communication system according to claim 1, wherein the wireless operating room communication system is synchronized on a first frequency channel for transmitting the video signals and the control signals, and
    wherein each of the wireless multiple device control unit, the wireless video transmitter unit, the at least one wireless surgical device and the wireless video display unit are configured to change to a second frequency channel when channel data capacity for the first frequency channel is not sufficiently capable of transmitting the video signals and the control signals, and electromagnetic interference provides a signal to noise ratio below a minimum tolerable ratio.

3. The wireless operating room communication system according to claim 1, wherein the wireless multiple device control unit, the wireless video transmitter unit and the at least one wireless surgical device are configured to provide high priority data protection for the control signals transmitted with the video signals and low priority video data protection for the video signals by prioritizing the video signals with most significant bits and lowest significant bits, so that the lowest significant bits of the video signal are lost to reduce the video signals transmitted while transmission of the control signals is maintained if channel characteristics deteriorate.

4. The wireless operating room communication system according to claim 3, wherein the wireless video transmitter unit outputs the video signal with a limited time delay to provide a low latency video signal transmission so that time delay in providing a video image to the wireless video display unit is less than 30% of the time required by the wireless video transmitter unit to obtain a frame from an image sensor of the endoscopic camera.

5. The wireless operating room communication system according to claim 1, wherein the wireless operating room communication system further comprises a wireless stored video transmission unit including a video transmitter for wireless transmission of stored video signals, the wireless stored video transmission unit including a reader for reading stored surgical video and surgical images, the reader providing at least one of the surgical video or surgical images to the video transmitter of the wireless stored video transmission unit for transmission therefrom, wherein the wireless stored video transmission unit operates on a different channel than the wireless video transmitter unit.

6. The wireless operating room communication system according to claim 5, wherein during system synchronization, the wireless operating room communication system determines and rates the characteristics of plural frequency channels and assigns a highest rated frequency channel as the different channel to the wireless video transmitter unit for transmission of camera video signals thereon and assigns another frequency channel to the wireless stored video transmission unit for transmission of pre-recorded video signals thereon.

7. The wireless operating room communication system according to claim 1, wherein the wireless operating room communication system is capable of providing system software upgrades to each of the wireless multiple device control unit, the wireless video transmitter unit, the at least one said surgical device and the wireless video display unit.

8. The wireless operating room communication system according to claim 1, wherein the wireless operating room communication system continuously monitors the signal characteristics of a frequency channel for the video signals transmitted by the wireless video transmitter unit, and when the signal to noise ratio is below a minimum value, switches the devices and the units of the operating room communication system to a different frequency channel.

9. The wireless operating room communication system according to claim 1, wherein the wireless video transmitter unit is integral with the endoscope camera disposed within a camera head secured to the endoscope.

10. The wireless operating room communication system according to claim 1, wherein said at least one wireless surgical device comprises at least one of an insufflator device, an electrocautery probe device, and an endoscope light source device.

11. A wireless operating room communication system comprising:
- a wireless stored video transmission unit including a transmitter for wireless transmission of video signals and a key input port, the wireless stored video transmission unit having a reader for reading stored surgical video and surgical images and for providing at least one of the surgical video or images to the transmitter;
- a portable wireless video display unit having a wireless video receiver for receiving wireless video signals and a key input port, the portable wireless video display unit having a battery for supplying power thereto; and
- a key device for insertion into the key input port of the wireless stored video transmission unit and the key input port of the wireless video display unit, the key device including data thereon for synchronizing the wireless video display unit to the wireless stored video transmission unit, wherein the surgical video or surgical images are transmitted by the wireless video transmission unit and received by the wireless video display unit for display thereon.

12. The wireless operating room communication system according to claim 1, wherein the video signals are free from data compression.

13. The wireless operating room communication system according to claim 1, wherein the wireless video transmitter unit is free from frame buffers for storing multiple frames of video image data.

14. The wireless operating room communication system according to claim 1, the at least one surgical device comprising surgical tools, each said surgical tool having a non-video transmitter and a receiver.

15. The wireless operating room communication system according to claim 1, wherein the at least one surgical device comprises an endoscope light source including the non-video transmitter and the receiver.

16. The wireless operating room communication system according to claim 11, further comprising:
- a wireless multiple device control unit including a non-video transmitter and a receiver;
- an endoscope camera and a wireless video transmitter unit for broadcasting video signals from the camera; and
- at least one wireless surgical device, said at least one surgical device including a non-video transmitter and a receiver.

17. The wireless operating room communication system according to claim 16, wherein the multiple device control unit and the at least one said wireless surgical device are configured to receive and synchronize with the video signals broadcast by the wireless video transmitter unit, and
   wherein the at least one wireless surgical device and the multiple device control unit are configured to transmit control signals on the same frequency channel as the video signals transmitted by said wireless video transmitter unit.

18. The wireless operating room communication system according to claim 17, wherein the wireless operating room communication system is synchronized on a first frequency channel for transmitting the video signals and the control signals, and
   wherein the wireless multiple device control unit, the wireless video transmitter unit and the at least one wireless surgical device are configured to change to a second frequency channel when channel data capacity for the first frequency channel is not sufficiently capable of transmitting the video signals and the control signals, and electromagnetic interference provides a signal to noise ratio below a minimum tolerable ratio.

19. The wireless operating room communication system according to claim 16, wherein the wireless video transmitter unit outputs the video signal from the camera with a limited time delay to provide a low latency video signal transmission so that time delay in providing a video image to the portable wireless video display unit is less than 30% of the time required by the wireless video transmitter unit to obtain a frame from an image sensor of the endoscopic camera.

20. The wireless operating room communication system according to claim 16, wherein said at least one wireless surgical device comprises at least one of an insufflator device and an electrocautery probe device.

* * * * *